United States Patent [19]

Cagnoni

[11] Patent Number: 5,609,877
[45] Date of Patent: Mar. 11, 1997

[54] TREATMENT OF THE ARTICULAR SYMPTOMS OF RHEUMATOID ARTHRITIS

[76] Inventor: Mario Cagnoni, 178, Via Bolognese, 50139 Firenze, Italy

[21] Appl. No.: 351,104

[22] Filed: Nov. 30, 1994

[51] Int. Cl.$^6$ ................. A61K 6/00; A61K 7/00
[52] U.S. Cl. ........................... 424/401; 424/422
[58] Field of Search ................. 424/401, 422; 514/825

[56] References Cited

U.S. PATENT DOCUMENTS 4,309,415  1/1982  Horrobin ..................... 424/85

FOREIGN PATENT DOCUMENTS 0605371  7/1994  European Pat. Off. .
8700432  1/1987  WIPO .
8807367  10/1988  WIPO .

OTHER PUBLICATIONS

Wei Wei et al. "Regulatory effects of pineal gland and melatonin on inflammatory and immune responses", Advances in Pineal Research vol. 7 pp. 1 131–136.

XU Shu–Yun et al. "Effects of total glucosides of paeony and moutan cortex on the functions of pineal gland in infolammatory–immune regulations in rats", Chinese Journal of Pharmacology vol. 8 No. 3, pp. 161–165, 1994.

Stanley K. West et al. "Melatonin Levels are Decreased in Rheumatoid Arthritis", Journal of Basics, vol. 3 No. 1, pp. 33–40, 1992.

M. Martinuzzo et al. "Melatonin effect on arachidonic acid metabolism to cyclooxygenase derivatives in human platelets", Journal of Pineal Research, vol. 11 No. ¾ pp. 111–115, 1991.

Marek Paelikowski et al. "Melatonin inhibits Prostaglandin E Release From the Medial Basal Hypothalamus of Pinealectomized Rats", Journal of Pineal Research, vol. 1 No. 4, pp. 317–321, 1984.

Catherine M. Leach et al. "A comparison of the inhibitory effects of melatonin and indomethacin on platelet aggregation and thromboxane release", Prostaglandins, vol. 20 No. 1, 1980.

James E. F. Reynolds "Martindale, The Extra Pharmacopoeia", The Pharmaceutical Press, pp. 22–24, 1989.

Ana M. Franchi et al. "Melatonin, 5–methoxytryptamine and some of their analogs as cyclooxygenase inhibitors in rat medial basal hypothalamus", Brain Research, vol. 3 No. 2, pp. 384–388, 1987.

*Primary Examiner*—Thurman K. Page
*Assistant Examiner*—Sharon Howard
*Attorney, Agent, or Firm*—Browdy and Neimark

[57] ABSTRACT

The present invention relates to the employment of melatonin in the preparation and use of pharmaceuticals effective in the treatment of the articular symptoms of rheumatoid arthritis.

11 Claims, No Drawings

TREATMENT OF THE ARTICULAR SYMPTOMS OF RHEUMATOID ARTHRITIS

FIELD OF THE INVENTION

The present invention concerns the field of rheumatology and more precisely relates to the use of melatonin (MLT) in the treatment of articular inflammatory symptoms.

BACKGROUND ART

The most common of the diseases characterized by acute and chronic inflammation of the joints is rheumatoid arthritis. As regards its etiology, none of the hypotheses proposed over time has ever found persuasive confirmation. Recently the etiopathogenetic hypothesis according to which the disease can be ascribed to the group of forms of hypersensitivity (the immune theory) has won the greatest agreement.

In the therapy of this disease, pharmaceuticals of various types are used with the object of controlling the inflammatory process and also to remedy the damage that the inflammatory process itself caused to the osteocartilaginous structures. Among these we have gold salts, antimalarials, penicillamine, and furthermore all the analgesic and steroid and nonsteroid anti-inflammatory pharmaceuticals. In particular, the symptomatic therapy is carried out by resorting to antiphlogistic drugs (nonsteroidal anti-inflammatory agents and cortisone compounds) and the base therapy using synthesized antimalarials, penicillamine, azathioprine, cyclophosphamide, gold salts, etc.

All these therapies, however, along with undoubtedly beneficial effects, create, to different degrees, undesired side effects. Such effects become more evident in all those forms which, like rheumatoid arthritis, require continuous therapy. In these degenerative inflammatory pathologies which, in the majority of cases, have a chronic course, the importance of finding an efficient pharmaceutical with scarce or no side effects is particularly felt.

Melatonin (N-acetyl-5-methoxytryptamine) is synthesized in the pineal body. It is derived from the hydroxylation and decarboxylation of tryptophan to 5-hydroxytryptamine (serotonin), and from the successive N-acetylation of the serotonin carried out by the enzyme N-acetyltransferase.

Melatonin is secreted rhythmically into the blood stream and distributed to the target cells to which it binds by means of specific binding sites. The circadian rhythm of melatonin levels is synchronized with light-dark alternation.

The activity of the N-acetyltransferase enzyme increases by 30 to 70 times during nighttime hours, and, consequently, melatonin reaches its maximum level between 24.00 and 04.00 h.

The synthesis of melatonin is promoted by noradrenergic stimulation by post-ganglionic sympathetic fibers which, at least in rodents terminate on beta-1 receptors.

Melatonin is metabolized in the brain and liver and is excreted in the urine. It functions as a neurotransmitter and neuromodulator and has a role of primary importance in the interaction of the neuroendocrine and immune systems.

No toxic effect following administration of melatonin has ever been recorded and, therefore, no contraindications exist for its use in human therapy.

Numerous studies have been conducted, also on healthy volunteers, to evaluate melatonin's effect as a synchronizer of sleep-wake rhythm.

Therapy with melatonin has been experimented in numerous and different pathological conditions, also at extremely high dosages. For example in Parkinson's disease, daily doses of melatonin of 6 gr. have been used without any damage, although without any demonstrable advantages.

Many clinical and experimental observations have suggested the existence of a relationship between the pineal body and neoplastic diseases and, more particularly, have shown an anti-proliferative activity of melatonin.

SUMMARY OF THE INVENTION

It has now been found, and this forms the object of the present invention, that melatonin constitutes an effective therapeutic means for the treatment of articular inflammatory diseases. This treatment is completely free of side effects.

With regard to inflammatory articular afflictions, the best results have been obtained with treatment via intra-articular injections. The commonly used dose in clinical experimentation has been 10 mg injected into the articulation. Nevertheless, lower and higher doses have proven effective. A range comprised between 5 and 30 mg has proved compatible both with regard to the beneficial effects and to the absence of undesired phenomena.

As the starting material, a lyophilized product, available in vials or phials, containing the peptide and an inert excipient was used, provided by the pharmacy of Dr. Ferrari (S. Lazzaro di Savena Bologna). At the time of use, the lyophilized product is diluted in water to make an injectable solution, in the proportion of 5 ml of water to every 10 mg of melatonin. It goes without saying that any other pharmaceutical form acceptable for melatonin is comprised within the scope of the present invention.

Experimental work

The effectiveness of therapy with melatonin has been demonstrated in a double-blind experiment with melatonin and placebo. 16 patients with RA and significant articular involvement were selected, with informed consent, for the experiment. The knee was chosen as the joint for the study.

The effectiveness of the melatonin therapy has been demonstrated by double-blind experiments versus placebo. 16 patients with rheumatoid arthritis and serious articular disease were selected. They expressly consented to the experiment. The knee joint was selected for experiment purpose.

In conformity with the double-blind scheme (melatonin versus placebo), 8 patients were treated with one dose of 10 mg of melatonin injected into the knee joint and 8 received intra-articular injections of placebo (5 ml of physiological solution). The clinical observations were carried out three, seven and fifteen days after the injection. As criteria, the Ritchie index and the Huskisson pain scale were chosen, with evaluation of pain at walking, at flexion and in supine position.

The Ritchie index is evaluated during the direct examination of the joint, which is compressed by the hand of the examiner.

The scale of values is as follows:

0=no pain

1=pain

2=pain and wince

3=pain, wince and retraction.

The Huskisson scale is of an analogical type and specifies the intensity of pain through a subjective evaluation with scores ranging from 1 to 10. In the period comprised between the first day following the injection and the fifteenth day, the patients noted daily the intensity of the pain according to the above-mentioned scale.

In tables 1 and 2 attached, the results obtained on the 16 treated patients are shown. The values relative to the Huskisson scale are, for the sake of brevity, only those which the patients recorded the third, seventh and fifteenth days of the treatment.

In relation to each of the clinical cases described above, the following provides details about the diagnosis, an evaluation of the effectiveness of the therapies in progress before the beginning of the treatment with melatonin and, finally, observations relative to the effect obtained with melatonin and with placebo.

TABLE 1

Melatonin treated patients

| Case no. | Initials | RITCHIE INDEX | | | | PAIN LEVEL (HUSKISSON) | | | | |
|---|---|---|---|---|---|---|---|---|---|---|
| | | Before | 3 days after | 7 days after | 15 days after | Position | Before | 3 days after | 7 days after | 15 days after |
| 1 | C.A. | 2 | 2 | 1 | 0 | S | 3 | 3 | 1 | 0.5 |
| | | | | | | F | 7 | 5 | 2 | 1 |
| | | | | | | D | 7 | 5 | 1 | 1 |
| 2 | F.T. | 3 | 2–3 | 1 | 1 | S | 3 | 2 | 1.5 | 1.5 |
| | | | | | | F | 8 | 6 | 2 | 2 |
| | | | | | | D | 8 | 8 | 2 | 2 |
| 3 | S.T. | 3 | 2 | 2 | 1 | S | 7 | 6 | 6 | 2 |
| | | | | | | F | 8 | 6 | 6 | 1.5 |
| | | | | | | D | 8 | 7 | 7 | 2.5 |
| 4 | V.A. | 2 | 1 | 0 | 1 | S | 2 | 1.5 | 1 | 1 |
| | | | | | | F | 2 | 1 | 0 | 1.5 |
| | | | | | | D | 5 | 3 | 1 | 2 |
| 5 | A.R. | 3 | 1–2 | 0 | 1 | S | 2 | 2 | 0.5 | 1 |
| | | | | | | F | 4 | 3 | 0 | 0 |
| | | | | | | D | 4 | 3 | 1.5 | 1.5 |
| 6 | F.F. | 3 | 2 | 1 | | S | 3 | 3 | 1 | 1.5 |
| | | | | | | F | 8 | 7 | 2 | 2.5 |
| | | | | | | D | 7–8 | 6–7 | 2 | 2 |
| 7 | M.S. | 2 | 2 | 0 | 1 | S | 2 | 1.5 | 0 | 1.5 |
| | | | | | | F | 2 | 2 | 1 | 1 |
| | | | | | | D | 4 | 2 | 1 | 1.5 |
| 8 | P.C. | 3 | 2–3 | 0 | 1 | S | 3 | 3 | 0 | 1 |
| | | | | | | F | 7 | 6 | 0 | 0 |
| | | | | | | D | 7 | 7 | 1 | 1.5 |

S = supine position
F = flexion
D = walking

TABLE 2

Placebo treated patients

| Case no. | Initials | RITCHIE INDEX | | | | PAIN LEVEL (HUSKISSON) | | | | |
|---|---|---|---|---|---|---|---|---|---|---|
| | | Before | 3 days after | 7 days after | 15 days after | Position | Before | 3 days after | 7 days after | 15 days after |
| 9 | A.V. | 2 | 2 | 2 | 3 | S | 4 | 4 | 4 | 5 |
| | | | | | | F | 6 | 5 | 4 | 6 |
| | | | | | | D | 6 | 6 | 5 | 6 |
| 10 | O.R. | 3 | 2 | 3 | 3 | S | 4 | 3 | 3 | 4 |
| | | | | | | F | 7 | 6 | 8 | 8 |
| | | | | | | D | 8 | 8 | 8 | 8 |
| 11 | I.F. | 2 | 2-3 | 2 | 2 | S | 2 | 2 | 3 | 3 |
| | | | | | | F | 9 | 7 | 8 | 8 |
| | | | | | | D | 9 | 9 | 8 | 8 |
| 12 | P.S. | 3 | 2 | 2 | 3 | S | 4 | 4 | 4 | 4 |

TABLE 2-continued

Placebo treated patients

| Case no. | Initials | RITCHIE INDEX | | | | PAIN LEVEL (HUSKISSON) | | | | |
|---|---|---|---|---|---|---|---|---|---|---|
| | | Before | 3 days after | 7 days after | 15 days after | Position | Before | 3 days after | 7 days after | 15 days after |
| | | | | | | F | 8 | 6 | 6 | 7 |
| | | | | | | D | 7 | 6 | 6 | 8 |
| 13 | A.C. | 2 | 2 | 2 | 1 | S | 5 | 4 | 4 | 3 |
| | | | | | | F | 8 | 6 | 6 | 6 |
| | | | | | | D | 8 | 7 | 7 | 8 |
| 14 | A.O. | 3 | 1 | 3 | 3 | S | 3 | 2 | 3 | 3 |
| | | | | | | F | 8 | 6 | 7 | 8 |
| | | | | | | D | 8 | 8 | 8 | 8 |
| 15 | F.D. | 2 | 3 | 2 | 2 | S | 3 | 2 | 2 | 2 |
| | | | | | | F | 8 | 7 | 5 | 7 |
| | | | | | | D | 7 | 8 | 7 | 7 |
| 16 | M.P. | 3 | 3 | 2 | 3 | S | 6 | 6 | 5 | 6 |
| | | | | | | F | 7 | 8 | 5 | 8 |
| | | | | | | D | 8 | 8 | 6 | 7 |

S = supine position
F = flexion
D = walking

Case no. 1—(MLT)
Initials: C.A. Age: 52 years Sex: female
Diagnosis: RA with polyarticular symptoms
Duration of the disease: 27 years
The patient had undergone, in the past, a clinical synovectomy on both knees. At the time of the initiation of the study, these joints had strong spontaneous pain which became accentuated during movement and with the pressure of the hand.
She was in treatment with 20 mg Piroxicam 20 and 8 mg 6-alpha-methylprednisolone with modest results; she had evident characteristic signs of osteoporosis (iatrogena).
Remarks: the response to the intra-articular therapy with MLT was satisfying and was maintained over time.

Case no. 2—(MLT)
Initials: F.T. Age: 68 years Sex: female
Diagnosis: RA with polyarticular symptoms
Duration of the disease: 20 years
The patient, over the course of the illness had undergone therapies with gold salts, steroids and penicillamine with varying results. She had gonarthritis, and at the time of the experiment had been taking ac. thiaprophenic acid 250 without appreciable results.
Remarks: optimum response to MLT. The beneficial effects were still present on the fifteenth day.

Case no. 3—(MLT)
Initials: S.T. Age: 64 years Sex: female
Diagnosis: RA with polyarticular symptoms
Duration of the disease: 8 years
The patients left knee was very achy and subject to pain, swollen and with conspicuous effusion.
She was in therapy, without any noteworthy effects with intra-muscular gold salts and diclofenac 50.
Remarks: good response to treatment with MLT. On the fifteenth day no significant reappearance of effusion could be found.

Case no. 4—(MLT)
Initials: V.A. Age: 76 years Sex: female
Diagnosis: RA with polyarticular symptoms
Duration of the disease: 22 years
The patient had been in treatment for many years with hydroxychloroquine. At the time of the clinical examination, she had considerable swelling of the left knee and spontaneous pain that became accentuated under load. She was taking 20 mg piroxicam.
Remarks: a good response to MLT which was still present on the fifteenth day.

Case no. 5—(MLT)
Initials: A.R. Age: 50 years Sex: female
Diagnosis: RA with polyarticular symptoms
Duration of the disease: 3 years
The patient had a particularly aggressive form of RA which, up to this time, had not obtained any considerable benefit from the base therapy.
The patient had strong pain in both knees, increasing with load on the right knee, in which the injection of MLT was carried out.
At the time of the experiment, the patient had been taking diclofenac 50.
Remarks: good and quick response to MLT that was still evident on the fifteenth day.

Case no. 6—(MLT)
Initials: F.F. Age: 55 years Sex: female
Diagnosis: RA with polyarticular symptoms
Duration of the disease: 16 years
The patient, over the course of the disease, had been subjected to numerous therapies with scarce success. The joint of the right knee appeared swollen and spontaneously achy, most of all under load. Considerable effusion was also present.
At the time the patient was taking 20 mg piroxicam and 4 mg 6-alpha-methylprednisolone with modest results.
Remarks: good results with MLT on the examination of the seventh and fifteenth days.

Case no. 7—(MLT)
Initials: M.S. Age: 48 years Sex: male
Diagnosis: RA with polyarticular symptoms
Duration of the disease: 6 years
The patient was in therapy with gold salts with fair results. The right knee was achy and subject to pain, and moderately swollen.
The patient was taking thiaprophenic acid 250 with modest results as far as concerns the gonarthritis.

Remarks: no response to MLT on the third day; optimum response on the seventh day and good response on the fifteenth day.

Case no. 8—(MLT)

Initials: P.C. Age: 62 years Sex: male

Diagnosis: RA with polyarticular symptoms

Duration of the disease: 16 years

The patient was in therapy with gold salts administered orally. The effects of the therapy were very modest. The right knee had considerable effusion which was partially removed at the time of the intra-articular injection, and was furthermore achy, particularly under load.

The patient was taking 20 mg piroxicam with modest effects.

Remarks: optimum response on the seventh and fifteenth days; only a fair response on the third day.

Case no. 9—(PL)

Initials: A.V. Age: 57 years Sex: female

Diagnosis: RA with polyarticular symptoms

Duration of the disease: 12 years

The patient was in treatment with gold salts taken orally with scarce results. The right knee was achy and swollen.

At the time, she was taking naproxen 500×2 with fair results.

Remarks: no appreciable variation after intra-articular injection, on the third and seventh days; slight deterioration on the fifteenth day.

Case no. 10—(PL)

Initials: O.R. Age: 42 years Sex: female

Diagnosis: RA with polyarticular symptoms

Duration of the disease: 8 years

The patient was in treatment with gold salts take orally, with scarce results and was also taking thiaprophenic acid 250.

The above-mention therapy did not significantly modify the gonarthritic picture present in the patient for quite some time.

Remarks: the intra-articular injection did not have any beneficial effect.

Case no. 11—(PL)

Initials: I.F. Age: 52 years Sex: male

Diagnosis: RA with polyarticular symptoms

Duration of the disease: 13 years

The patient had a particularly aggressive form of RA that proved resistant to the different types of base therapies practiced.

In particular, achy and subject to pain swelling of the left knee was present.

The patient was taking, with scarce effects, thiaprophenic acid 250.

Remarks: no significant effect was found in any of the three examinations.

Case no. 12—(PL)

Initials: P.S. Age: 50 years Sex: male

Diagnosis: RA with polyarticular symptoms

Duration of the disease: 15 years

The patient responded well to the base therapies which, nevertheless, had to be suspended due to the appearance of undesired side effects.

The joint of the left knee was achy under load.

The patient was taking, with modest results, naproxen 500×2.

Remarks: no significant clinical results were found.

Case no. 13—(PL)

Initials: P.S. Age: 51 years Sex: female

Diagnosis: RA with polyarticular symptoms

Duration of the disease: 8 years

The patient had an oligoarticular form of the disease. A considerable involvement of the joint of the left knee was present.

The patient was taking 20 mg piroxicam with modest results

Remarks: no beneficial effect was found following treatment with placebo.

Case no. 14—(PL)

Initials: A.Q. Age: 60 years Sex: female

Diagnosis: RA with polyarticular symptoms

Duration of the disease: 20 years

The patient had been subjected, with modest results, to numerous base therapies. At the time of the experiment, she had achy and subject to pain swelling in both knees. She was taking, with modest and transitory results, 8 mg 6-alpha-methylprednisolone.

Remarks: good response on the third day and no positive effect on the seventh and fifteenth days.

Case no. 15—(PL)

Initials: F.D. Age: 51 years Sex: male

Diagnosis: RA with polyarticular symptoms

Duration of the disease: 9 years

The patient suffered from RA that was still in the acute phase.

He had been taking for some time, without significant effects, hydroxychloroquine. He had a clear involvement of the left knee, effusion and subject to pain swelling.

He was taking 20 mg piroxicam.

Remarks: no significant effect after intra-articular injection of placebo.

Case no. 16—(PL)

Initials: M.P. Age: 57 years Sex: female

Diagnosis: RA with polyarticular symptoms

Duration of the disease: 20 years

The patient had been subjected to base therapies with long periods of well-being followed by deteriorations of the symptomatology. At the time of the experiment, she had a prevalently right gonarthritic picture.

The intra-articular injection with placebo was carried out on the joint of the right knee.

The patient was taking naproxen 500×2 with scarce results.

Remarks: no significant variation of the symptomatology followed intra-articular injection of placebo.

On the basis of the results obtained, it can be affirmed that melatonin, injected into the joint of the knee affected by alterations of a rheumatoid type, produced optimum clinical results.

Treatment with melatonin, in fact, caused a considerable reduction of both subjective and provoked (Ritchie index) pain, in supine position, during movement and in conditions of flexion (Huskisson pain scale).

The effect of the therapy was still present, in the majority of the cases, 15 days after the beginning of the treatment. From various experiences, though not controlled, with patients affected by RA, it appears that therapy consisting in the oral administration of 20 mg a day of melatonin in tablets had a beneficial effect.

Pharmaceuticals containing melatonin which can be used for the treatment of rheumatoid arthritis according to the present invention can be in the form of a vial for intra-articular or intra-muscular injection, or in the form of phials for oral administration of tablets, pills or capsules, and include also the usual pharmaceutical vehicles and adjuvants compatible with well-known pharmaceutical technology.

Variations and/or modifications can be brought to the above-described therapeutic scheme without departing from the spirit and scope of the invention itself. The examples provided are given only for the purpose of illustration and are not limitative of the invention itself.

I claim:

1. A method of treatment of articular inflammatory diseases comprising treating a patient in need thereof with an effective amount of an agent consisting essentially of melatonin.

2. A method of treatment of articular inflammatory diseases, comprising administering melatonin through intra-articular injection at a dose for a single injection of between 5 and 30 mg.

3. The method according to claim 2, wherein said dose is about 10 mg.

4. The method according to claim 1, wherein the melatonin is administered orally at a dose comprised between 10 and 20 mg daily.

5. The method according to claim 1, wherein said articular inflammatory disease is rheumatoid arthritis.

6. A pharmaceutical composition consisting essentially of malatonin as an active agent in an amount sufficient for the treatment of articular inflammatory disease and a pharmaceutically acceptable carrier.

7. A pharmaceutical composition according to claim 6 wherein said melatonin is present in an amount effective in the treatment of rheumatoid arthritis.

8. A pharmaceutical composition according to claim 6 in the form of a single dosage unit of 5–30 mg of melatonin suitable for intra-articular administration.

9. A pharmaceutical composition according to claim 6 in the form of a daily dosage unit of 5–30 mg of melatonin suitable for oral administration.

10. A pharmaceutical composition according to claim 8, wherein said single dosage unit comprises about 10 mg of said melatonin.

11. A pharmaceutical composition according to claim 9, wherein said daily dosage unit comprises about 10 mg of said melatonin.

* * * * *